United States Patent [19]

Gootjes

[11] 4,265,894
[45] May 5, 1981

[54] PIPERAZINE DERIVATIVES

[75] Inventor: Johan Gootjes, Heerhugowaard, Netherlands

[73] Assignee: Gist Brocades, N.V., Delft, Netherlands

[21] Appl. No.: 90,257

[22] Filed: Nov. 1, 1979

Related U.S. Application Data

[62] Division of Ser. No. 860,460, Dec. 14, 1977, Pat. No. 4,202,896.

[30] Foreign Application Priority Data

Dec. 14, 1976 [GB] United Kingdom ............... 52223/76

[51] Int. Cl.³ .................. A61K 31/495; C07D 295/02
[52] U.S. Cl. .................................... 424/250; 542/470; 544/391; 544/397
[58] Field of Search ......................... 542/470; 424/250

Primary Examiner—Donald G. Daus
Assistant Examiner—James H. Turnipseed
Attorney, Agent, or Firm—Robert E. Burns; Emmanuel J. Lobato; Bruce L. Adams

[57] ABSTRACT

Piperazine derivatives of the general formula

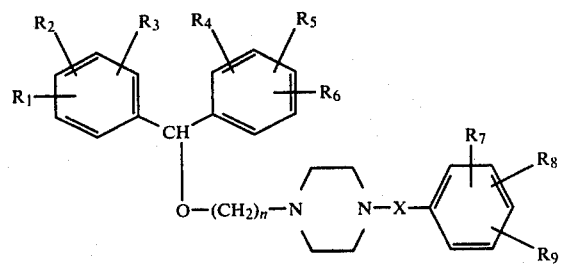

wherein $R_1$–$R_9$ are the same or different and each represents a hydrogen or halogen atom or a lower alkyl or lower alkoxy group, n is 2 or 3 and X represents a group $(CH_2)_m$ (in which m is 1, 2, 3 or 4) or a group —$CH_2$—CH=CH—, having methylene linked to the piperazine group, and acid addition and quaternary ammonium salts thereof, are described.

The compounds exhibit a strong specific dopaminergic activity.

Also described are methods for their preparation and use as therapeutic agents in the form of therapeutic compositions.

21 Claims, No Drawings

PIPERAZINE DERIVATIVES

This is a divisional of application Ser. No. 860,460, filed Dec. 14, 1977, now U.S. Pat. No. 4,202,896.

This invention relates to new, therapeutically active piperazine derivatives, to processes for their preparation and to pharmaceutical compositions containing them.

The new piperazine derivatives of the present invention are those compounds of the general formula:

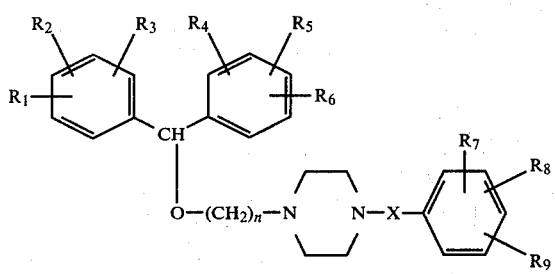

Wherein $R_1$–$R_9$ are the same or different and each represents a hydrogen or halogen (preferably fluorine, chlorine or bromine) atom or a lower alkyl (preferably methyl) or lower alkoxy (preferably methoxy) group, n is 2 or 3 and X represents a group $(CH_2)m$ (in which m is 1, 2, 3 or 4), or a group —$CH_2$—$CH$=$CH$—, having methylene linked to the piperazine group, and acid addition and quaternary ammonium salts thereof.

The terms "lower alkyl" or "lower alkoxy" as used in this specification and the accompanying claims refer to groups with at most six and preferably not more than 4 carbon atoms. In view of pharmacological properties and chemical considerations (ease of synthesis, availability of starting materials) the following meanings of the symbols are preferred.

$R_1$–$R_6$: hydrogen or one or two of them fluorine or methoxy, both preferably in the para position and the others hydrogen;

$R_7$–$R_9$: all hydrogen or one of them chlorine or fluorine, preferably in the para position, and the other two hydrogen;

X: —$CH_2$—$CH$=$CH$— or $(CH_2)_3$;

n: 2.

In view of their pharmacological properties the following compounds are particularly preferred:

1-[2-(diphenylmethoxy)ethyl]-4-(3-phenyl-2-propenyl)-piperazine,
1-[2-[(4-methoxyphenyl)phenylmethoxy]ethyl]-4-(3-phenyl-2-propenyl) piperazine,
1-[2-[(4-fluorophenyl)phenylmethoxy]ethyl]-4-(3-phenyl-2-propenyl) piperzine,
1-[2-[bis(p-fluorophenyl)methoxy]ethyl]-4-(3-phenyl-2-propenyl)piperazine
1-[2-[bis-(4-fluorophenyl)methoxy]ethyl]-4-[3-(4-fluorophenyl)-2-propenyl]piperazine,
1-[2-[bis(4-fluorophenyl)methoxy]ethyl]-4-[3-(4-chlorophenyl)-2-propenyl]piperazine and
1-[2-[bis(4-fluorophenyl)methoxy]ethyl]-4-(3-phenylpropyl)piperazine and their acid addition and quaternary ammonium salts.

The piperazine derivatives of general formula I possess useful pharmacological properties that resemble those of bromocriptine. They show a strong specific dopaminergic activity and low toxicity and are therefore useful in the treatment of Parkinson's disease and pathological conditions associated with hyperprolactinemia (galactorrhea, excessive puerperal lactation, hypogonadism, infertility) and with excessive growth hormone secretion (acromegaly). They also show anticholinergic activity, which enhances their usefulness in the treatment of Parkinson's disease. The dopaminergic activity was assessed both in animal experiments (stimulation, stereotypy, bizarre social behaviour) and in virto (inhibition of dopamine re-uptake by striatal synaptosomes). The doses to be administered will depend on the disorder to be treated. Suitable daily oral doses for human adults are (i) in the case of parkinsonism: 50–200 mg; (ii) in acromegaly: 20–40 mg; and (iii) in prolactine-induced disorders: 5–25 mg.

According to a feature of the invention, the piperazine derivatives of general formula I are prepared by the process which comprises reacting an ether of the general formula:

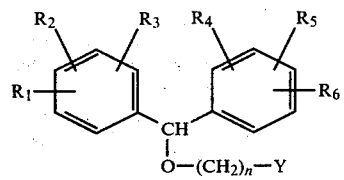

[wherein Y represents a halogen (preferably chlorine or bromine) atom or another acid residue of a reactive ester such as toluene-p-sulphonyloxy and the other symbols are as hereinbefore defined] with a piperazine derivative of the general formula:

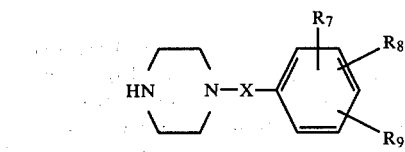

wherein $R_7$, $R_8$, $R_9$ and X are as hereinbefore defined. The reaction is preferably carried out by refluxing the reactants in an inert organic solvent, such as toluene or methyl isobutyl ketone, the latter being more suitable in view of its polar character.

It is advantageous to carry out the reaction in the pressure of a base, for example potassium carbonate or a tertiary amine (e.g. triethylamine), and—when Y in the compound of general formula II is chlorine or bromine—to add some potassium iodide.

The piperazine derivatives of general formula III may be prepared by reacting 1-formylpiperazine with a compound of the general formula:

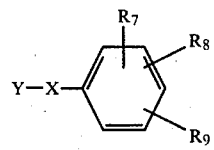

(wherein $R_7$, $R_8$, $R_9$, X and Y are as hereinbefore defined) and removing the formyl group from the resulting compound using, for example, the procedure described by T. Irikura et al. J. Med. Chem. 1968, 11(4), 801—, i.e. by treatment with 30% aqueous sodium hydroxide and heating the mixture at 90° to 100° C. for a number of hours.

Alternatively, the piperazine derivatives of general formula III may be prepared by reacting piperazine (preferably in excess) with an aldehyde of the general formula:

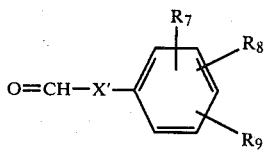

(wherein X' represents a direct bond or a grouping —$CH_2$—, —$CH_2$—$CH_2$— or —CH=CH— and $R_7$, $R_8$ and $R_9$ are as hereinbefore defined), and reducing the resultant compound. The reaction is preferably effected in an inert organic solvent medium. Preferably piperazine is reacted with the aldehyde of general formula V under reduction conditions that are preferably achieved by a catalytic hydrogenation using, for example, Raney nickel as a catalyst, or by sodium cyanoborohydride.

According to another feature of the invention, the piperazine derivatives of general formula I are prepared by the process which comprises reacting a compound of the general formula:

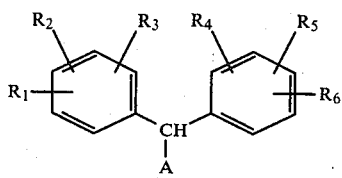

[wherein the symbols $R_1$, $R_2$, $R_3$, $R_4$, $R_5$ and $R_6$ are as hereinbefore defined, and A represents a hydroxy radical, a halogen (preferably chlorine or bromine) atom, or a group OM, in which M represents an alkali metal (preferably potassium or sodium)atom] with a compound of the general formula:

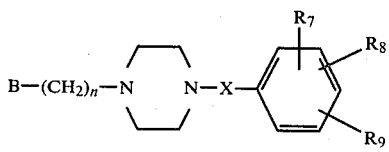

wherein $R_7$, $R_8$, $R_9$, n and X are as hereinbefore defined, and B represents: (i) a hydroxy radical or a halogen atom when A represents a hydroxy radical, or (ii) a hydroxy radical or a group OM (M being as hereinbefore defined) when A represents a halogen atom, or (iii) a halogen atom when A represents a group OM, M being as hereinbefore defined.

In most cases it is preferred to carry out the reaction in an inert organic solvent, for example benzene or toluene. In some instances, particularly when the compound of formula VI is a benzhydryl chloride, the reaction also proceeds smoothly without a solvent. Advantageous reaction conditions are furthermore—when A and B are both hydroxy radicals: reduced pressure and the presence of an acid that is not volatile at the reaction temperature, e.g. toluene-p-sulphonic acid;—when one of A and B is a hydroxy radical and the other is a halogen atom: the use of an excess of the piperazine derivative of general formula VII, or of a different basic agent such as sodium carbonate or a tertiary amine, e.g. triethylamine.

The compounds of general formula VII may be prepared by reacting 2-(piperazin-1-yl)ethanol or 3-(piperazin-1-yl)propanol with an aldehyde of general formula V and reducing the compound obtained in a similar manner as hereinbefore described for the preparation of piperazine derivatives of formula III, and optionally converting the hydroxy radical in the compound obtained of the general formula:

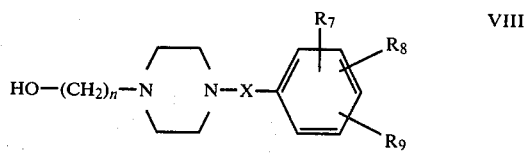

(wherein $R_7$, $R_8$, $R_9$, n and X are as hereinbefore defined) into a halogen atom or a group OM, M being as hereinbefore defined.

The conversion of the hydroxy radical into a halogen atom may be effected by reacting the compound of general formula VIII with a thionyl halide.

The hydroxy radical may be converted into a group OM by reacting the compound of general formula VIII with an alkali metal or an alkali metal hydride, dissolved or suspended in an inert organic solvent, e.g. benzene or toluene.

According to another feature of the invention, the piperazine derivatives of general formula I are prepared by the process which comprises reacting a compound of the general formula:

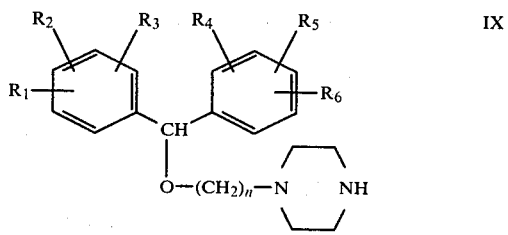

(wherein the various symbols are as hereinbefore defined) with a compound of general formula IV or V, and reducing—when the reactant is of general formula V—the intermediate product obtained.

The reaction between compounds of general formulae IX and IV is preferably carried out under the conditions hereinbefore described for the reaction of an ether of general formula II with a piperazine derivative of general formula III. The reaction between compounds of general formulae IX and V is preferably carried out under the conditions hereinbefore described for the preparation of compounds of general formula III by the reaction of piperazine with an aldehyde of general formula V.

According to another feature of the invention, the piperazine derivatives of general formula I are prepared by reducing a compound of the formula:

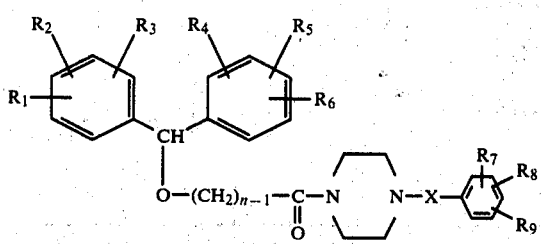

X (wherein the various symbols are as hereinbefore defined) in a manner known for the reduction of amides and hydrolysing the intermediate product obtained. Preferably the reduction is carried out in an inert organic solvent, such as diethyl ether or tetrahydrofuran, with a reducing agent such as lithium aluminium hydride. (cf. Chem. Soc. Rev. 5, 23–50 (1976). The amide starting materials of formula X may be prepared by reacting a compound of the formula

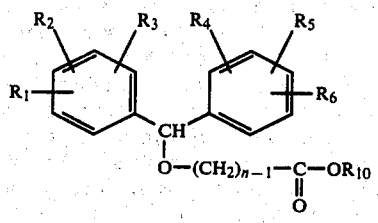

XI

1ps (wherein $R_{10}$ represents a lower alkyl (preferably methyl or ethyl) group and the other symbols are as hereinbefore defined) with a compound of formula III, preferably by refluxing the reactants in an inert organic solvent, such as benzene or xylene.

According to another feature of the invention, the piperazine derivatives of general formula I in which X is other than methylene, are prepared by reducing a compound of the formula

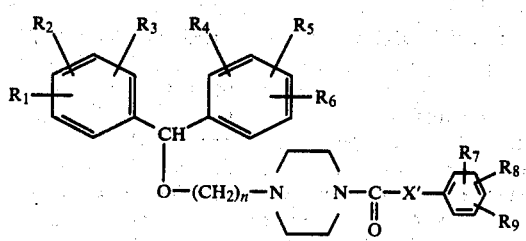

XII (wherein the various symbols are as hereinbefore defined) in a manner known for the reduction of amides and hydrolysing the intermediate product obtained. Preferred reaction conditions are as described for the reduction of compounds of formula X.

The amide starting materials of formula XII may be prepared by reacting a compound of formula IX with a compound of the formula

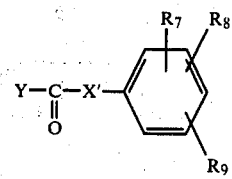

XIII (wherein the various symbols are as hereinbefore defined) preferably by refluxing the reactants in an inert organic solvent, such as benzene or toluene.

According to another feature of the invention the compounds of formula I in which X is a trimethylene group are prepared by reducing a corresponding compound in which X is a group —$CH_2$—CH=CH—. The reduction is suitably effected by hydrogenation in the presence of a metal catalyst such as platinum, paladium or Raney Nickel or by sodium amalgam. The reduction is preferably carried out in an organic solvent such as ethanol.

The free bases of general formula I may be converted into acid addition and quaternary ammonium salts by methods known per se. (By the term "methods known per se" is meant methods heretofore used or described in the chemical literature). The base may, for instance, be dissolved in an inert organic solvent, such as diethyl ether, and the desired acid addition salt, e.g. maleate or hydrochloride, may be precipitated by adding an ethereal solution of the appropriate acid. For the preparation of a quaternary ammonium salt, the base is reacted with, for example, an alkyl halide or sulphate at a moderate temperature in a polar organic solvent such as acetone.

The preparation of salts of strong acids should be carried out cautiously as the compounds tend to decompose at a pH below 2.

The preparation of piperazine derivatives of general formula I by processes of the invention is illustrated by the following Examples.

EXAMPLE 1

A mixture of 10.45 g (0.052 mole) of 1-cinnamylpiperazine, 29.2 g (0.104 mole) of bis(p-fluorophenyl)methyl-2-chloroethyl ether, 12.5 g (0.09 mole) of potassium carbonate, 2 g (0.012 mole) of potassium iodide and 250 ml of methyl isobutyl ketone was refluxed for 24 hours. The precipitate was filtered off and the filtrate was concentrated by evaporation of the solvent. Water and diethyl ether were added to the residue, the ethereal phase was separated off and dried over sodium sulphate. Then an ethereal maleic acid solution was added until the reaction mixture was acidic. The resulting precipitate was filtered off and recrystallized from a mixture of isopropyl alcohol and diethyl ether. 1-{2-[Bis(p-fluorophenyl)methoxy]ethyl}-4-(3-phenylprop-2-enyl)piperazine maleate (1:2) was obtained. It melted at 192°–194° C. The hydrochloride (1:2) melts at 211.5°–212° C.

EXAMPLE 2

Following the procedure of Example 1, but substituting the bis (p-fluorophenyl)methyl 2-chloroethyl ether by equivalent amounts of the appropriate starting material, the following compounds of formula I were prepared

| R$_1$ | R$_4$ | R$_3$,R$_5$,R$_6$,R$_7$,R$_8$,R$_9$ | X | n | Melting point (°C.) | cryst. solvent |
|---|---|---|---|---|---|---|
| 4-CH$_3$O | H | H | —CH$_2$—CH=CH— | 2 | 177.5 | a |
| 4-F | 4-F | H | —CH$_2$—CH=CH— | 3 | 195.5 | b | a = dimethylformamide and methanol
b = dimethylformamide and diethyl ether

EXAMPLE 3

A mixture of 1 g (0.003 mol) of 1-[2-[bis(4-fluorophenyl)methoxy]ethyl]piperazine, 0,4 g (0.003 mol) of 3-phenyl-2-propenal, 0,2 g of sodium cyanoborohydride and 15 ml of methanol was stirred for 4 hours at room temperature. Then 14 ml of 0,5 N hydrochloric acid were added and the mixture was stirred for another hour at room temperature. The methanol was distilled off and the residue was made alkaline with dilute aqueous sodium hydroxide solution and extracted with diethyl ether. The extract was dried over sodium sulphate and an ethereal solution of maleic acid was added. The precipitate was filtered off and crystallized from a mixture of methanol and dimethylformamide.

1-[2-[Bis(p-fluorophenyl)methoxy]ethyl]-4-cinnamylpiperazine maleate (1:2) was obtained. Melting point 192°–194° C.

1-[2-[Bis(4-fluorophenyl)methoxy]ethyl]piperazine, used as a starting material, was prepared as follows.

To a refluxing mixture of 52.0 g (0.6 mol) of piperazine and 55.3 g (0.4 mol) of potassium carbonate in 150 ml of toluene, 56.6 g (0.2 mol) of bis(p-fluorophenyl)-methyl 2-chloroethyl ether were slowly added dropwise. Subsequently the reaction mixture was refluxed for another 5 hours. The reaction mixture was then washed thoroughly with water and concentrated. To the residue a solution of maleic acid in diethyl ether was added and the precipitate formed was filtered off and crystallized from a mixture of methanol, dimethylformamide and diethyl ether. Melting point 159°–161° C.

EXAMPLE 4

A mixture of 5 g (0.02 mole) of 4-(3-phenyl-2-propenyl)-1-piperazine-ethanol (West German patent application No. 1.191.024) and 2.7 g (0.01 mole) of 4,4'-dichlorobenzhydryl chloride was heated for half an hour at 160° C. After being cooled to 100° C., the reaction mixture was poured into water and extracted with diethyl ether. The extract was washed with water and dried over sodium sulphate. To the solution obtained an ethereal solution of maleic acid in diethyl ether was added until the solution was acidic. The precipitate was filtered off and dried in vacuo at 60° C. Examination of the substance by thin-layer chromatography revealed the presence of piperazine starting material. This was removed by stirring the substance with water of circa 50° C. The solid was again filtered off and dried and crystallized from a mixture of methanol and dimethylformamide. 1-[2-[Bis(4-chlorophenyl)methoxy]ethyl]-4-(3-phenyl-2-propenyl) piperazine maleate (1:2) was obtained. Melting point 201° C.

EXAMPLE 5

In a similar manner as described in Example 4, using the appropriate starting materials, the following compounds of formula I were prepared (R$_2$,R$_3$,R$_5$,R$_7$,R$_8$,R$_9$ = H, X = —CH$_2$—CH=CH—, n = 2)

| R$_1$ | R$_2$ | R$_4$ | R$_5$ | R$_6$ | Melting point (°C.) | Purification |
|---|---|---|---|---|---|---|
| 4-CH$_3$ | H | H | H | H | 191 | a |
| 4-F | H | H | H | H | 193 | a |
| 4-F | H | 4-Cl | H | 2-Cl | 187 | b |
| H | 3-CH$_3$O | H | 3-Br | H | 182 | b | a crystallization from a mixture of methanol and dimethylformamide.
b after drying, the ethereal extract was concentrated by evaporation of the solvent. The residue was purified by chromatography over a silicagel column with a mixture of chloroform, ethyl acetate, methanol and ammonia (50:50:1:0.2) as the eluent. To the desired fraction ethereal maleic acid was added. The precipitate was crystallized from a mixture of methanol and dimethylformamide.

EXAMPLE 6

A solution of 6 g of 1-[(diphenylmethoxy)acetyl]-4-(3-phenyl-2-propenyl) piperazine in 100 ml of anhydrous diethyl ether was added dropwise at room temperature to a mixture of 1 g of lithium aluminum hydride and 150 ml of anhydrous diethyl ether. The mixture was refluxed for one hour and then cooled and decomposed by a mixture of tetrahydrofuran and water. The organic layer was separated off and the solvents were distilled off. The residue was dissolved in diethyl ether. The solution was dried over sodium sulphate, after which maleic acid in diethyl ether was added until the liquid was acidic. The precipitate was filtered off and crystallized from a mixture of methanol and dimethylformamide. The thin layer chromatogram revealed an impurity. The substance was therefore stirred with water of 50° C. and then filtered off and dried in vacuo at 60° C. 1-[2-(Diphenylmethoxy)ethyl]-4-(3-phenyl-2-propenyl) piperazine maleate (1:1) was obtained. Melting point 191° C.

1-[(Diphenylmethoxy)acetyl]-4-(3-phenyl-2-propenyl) piperazine, used as a starting material, was prepared as follows.

A solution of 12.8 g (0.05 mol) of (diphenylmethoxy acetic acid methyl ester (CA 43, 5018 h) en 10.1 g (0.05 mol) of 1-(3-phenyl-2-propenyl) piperazine in 200 ml of anhydrous xylene was refluxed for 26 hours. The reaction mixture was cooled and then the solvent was distilled off. The residue was subjected to column chromatography (silicagel, eluent: chloroform/ethyl acetate/methanol/ammonia 25:25:1:0.5). To the appropriate fraction ethereal maleic acid was added. The precipitate was filtered off and crytallized from a mixture of methanol and dimethylformamide. The maleate (1:1) obtained had a melting point 178,5° C. For use as a starting material, as described above, the salt was reconverted to the free base.

EXAMPLE 7

To a suspension of 1.5 g (0.0375 mol) of lithium aluminiumhydride in 75 ml of diethyl ether, a solution of 8 g (0.017 mol) of 1-[2-[bis(4-fluorophenyl)methoxy]ethyl]-4-[3-(4-methylphenyl)-1-oxo-2-propenyl] piperazine in 75 ml of diethyl ether was added dropwise with stirring. The mixture was refluxed for 2 hours and it was then cooled to 0° C. and decomposed with a mixture of water and tetrahydrofuran. The solid was filtered off and maleic acid in diethyl ether was added to the filtrate until it was acidic. The precipitate was filtered off and crystallized from a mixture of methanol and dimethylformamide. 1-[2-[Bis(4-fluorophenyl)methoxy]ethyl]-4-[3-(4-methylphenyl)-2-propenyl]piperazine maleate (1:2) was obtained. Melting point 193.5°–194.0° C.

The starting material was prepared as follows. A solution of 4.5 g (0.025 mol) of 3-(4-methylphenyl)-2-propenoyl chloride (R. F. Silver, Can. J. Chem. 45, 1001-6 (1967)) in 50 ml of anhydrous toluene was added dropwise at room temperature to a solution of 16.6 g (0.05 mol) of 1-[2-[bis(4-fluorophenyl)methoxy]ethyl]piperazine in 100 ml of anhydrous toluene. The mixture was refluxed for one hour and then cooled, washed with water, dried and concentrated. The residue was dissolved in diethyl ether, ethereal maleic acid was added and the precipitate was filtered off and crystallized from methanol. 1-[2-[Bis(4-fluorophenyl)methoxy]ethyl]-4-[3-(4-methylphenyl)-1-oxo-2-propenyl]piperazine maleate (1:1) was obtained. Melting point 172.0°–172.5° C. For use as a starting material, the salt was converted in the free base.

EXAMPLE 8

Following the procedure of Example 7, but using the following starting materials:
a.   1-[2-[bis(4-fluorophenyl)methoxy]ethyl]-4-[3-(4-chlorophenyl)-1-oxo-2-propenyl]piperazine
b.   1-[2-[bis(4-fluorophenyl)methoxy]ethyl]-4-[3-(2,5-dimethoxyphenyl)-1-oxo-2-propenyl]piperazine;
c.   1-[2-[bis(4-fluorophenyl)methoxy]ethyl]-4-[3-(4-methoxyphenyl)-1-oxo-2-propenyl]piperazine The following compounds were prepared:
a.   1-[2-[bis(4-fluorophenyl)methoxy]ethyl]-4-[3-(4-chlorophenyl)-2-propenyl]piperazine maleate (1:2), melting point 187.5° C.;
b.   1-[2-[bis(4-fluorophenyl)methoxy]ethyl]-4-[3-(2,5-dimethoxyphenyl)-2-propenyl]piperazine maleate (1:2), melting point 189.0°–189.5° C.
c.   1-[2-[bis(4-fluorophenyl)methoxy]ethyl]-4-[3-(4-methoxyphenyl)-2-propenyl]piperazine maleate (1:2). Melting point 186.5°–188.0° C.

The starting materials were prepared in a similar way as described for the starting material in Example 7.

EXAMPLE 9

To a mixture of 6 g (0.018 mol) of 1-[2-[bis(4-fluorophenyl)methoxy] ethyl]piperazine (prepared as described in Example 3) and 3 g of potassium carbonate powder in 50 ml of ethanol, 3.6 g (0.018 mol) of (3-bromopropyl) benzene (G. O. Aspinall et al., J. Chem. Soc. 1950, 743) was added dropwise at room temperature. The mixture was then slowly heated and refluxed for 3 hours. The reaction mixture was filtered and the filtrate was concentrated. The residue was taken up in diethyl ether, undissolved matter was filtered off and ethereal maleic acid was added until the liquid reacted acidic. The percipitate was filtered off and crystallized from a mixture of methanol and dimethylformamide. 1-[2-[Bis(4-fluorophenyl)methoxy]ethyl]-4-(3-phenylpropyl)piperazine maleate (1:2) was obtained. Melting point 185.0°–185.5° C.

EXAMPLE 10

Folloring the procedure of Example 9, but substituting an equivalent amount of 1-(3-chloro-1-propenyl)-4-fluorobenzene (German Pat. appl. 1.929.330) for the (3-bromopropyl) benzene, 1-[2-[bis(4-fluorophenyl)methoxy]ethyl]-4-[3-(4-fluorophenyl)-2-propenyl]piperazine maleate (1:2) was prepared. Melting point 189.0° C.

EXAMPLE 11

To a mixture of 6 g (0.018 mol) of 1-[2-[bis(4-fluorophenyl)methoxy]ethyl]piperazine (prepared as described in Example 3) and 3 g of potassium carbonate powder in 50 ml of ethanol, 3.1 g (0.018) of benzylbromide were added dropwise at room temperature. The reaction mixture was then slowly heated and refluxed for 3 hours. Subsequently another 3.1 g (0.018 mol) of benzylbromide were added dropwise at room temperature. The mixture was refluxed for 1,5 hours, cooled and filtered. The solvent was distilled off and the residue was purified by column chromatography (silicagel) with a mixture of chloroform and ethyl acetate (1:1) as the eluent. A solvent of maleic acid in diethyl ether was added to the desired eluate fraction, the precipitate was filtered off and crystallized from a mixture of methanol and dimethylformamide. 1-[2-[Bis(4-fluorophenyl)methoxy]ethyl]-4-(phenylmethyl)piperazine maleate (1:2) was obtained. Melting point 201.5°–202.5° C.

EXAMPLE 12

To a mixture of 5 g (0.02 mol) of 4-(3-phenyl-2-propenyl)-1-piperazine-ethanol (C.A.63 P 5660f) and 4 g (0.02 mol) of 4-fluorobenzylhydrol in 100 ml of toluene and 30 ml of dimethylformamide, 8 g of toluene-p-sulfonic acid were added. The mixture was refluxed with stirring for one hour, the water formed being distilled off azeotropically. The reaction mixture was then cooled and poured into dilute ammonia. The organic phase was separated off and the solvent was distilled off. The residue was purified by chromatography through a silicagel column with chloroform/ethylacetate/methanol/ammonia (25:25:1:0.5) as the eluent. The desired fraction was converted into the maleate by addition of ethereal maleic acid. The precipitate was filtered off and crystallized from a mixture of methanol and dimethylformamide. 1-[2-[(4-Fluorophenyl)phenylmethoxy]ethyl]-4-(3-phenyl-2-propenyl)piperazine maleate (1:2) was obtained. Melting point 193° C.

EXAMPLE 13

7.5 g (0.03 mol) of 4-(3-phenyl-2-propenyl)-1-piperazineethanol were added to a solution of 0.7 g (0.03 at) of sodium in 100 ml of methanol. Following evaporation of the methanol, 100 ml of anhydrous xylene were added to the residue. About 25 ml of xylene was distilled off to effect azeotropic removal of remaining methanol. The mixture was then refluxed and a solution of 6.5 g (0.03 mol) of 4-methylbenzhydrychloride in 50 ml of xylene was added dropwise in the course of one hour. After six hours refluxing, the reaction mixture was cooled, water was added and the organic layer was separated off and concentrated. The residue was dissolved in diethyl ether and the solution was acidified with ethereal maleic acid. The precipitate was filtered off and dried and stirred with warm water to remove remaining amine starting material. Finally, the substance was again filtered off and dried in vacuo at 60° C. 1-[2-[(4-Methylphenyl)phenylmethoxy]ethyl]-

4-(3-phenyl-2-propenyl)piperazine maleate (1:2). Melting point 191° C.

EXAMPLE 14

2 g of 60% sodium hydride in paraffin oil were added to a solution of 10 g (0.05 mol) of 4-methylbenzhydrol in 100 ml of anhydrous xylene. The reaction mixture was refluxed for half an hour and then 12.7 g (0.05 mol) of 1-(2-chloroethyl)-4-(3-phenyl-2-propenyl)piperazine (German Pat. appl. 2.431.178) in 50 ml of xylene were added dropwise. The reaction mixture was refluxed for another three hours and then cooled and poured into water. The organic layer was separated off, washed with water and concentrated. The residue was purified by column chromatography (Silicagel) with chloroform/ethylacetate/methanol/ammonia (25:25:1:0.5) as the eluent which yielded 1-[2-[(4-Methylphenyl)phenylmethoxy]ethyl]-4-(3-phenyl-2-propenyl)piperazine.

EXAMPLE 15

A mixture of 17.2 g. (0.07 mole) 2-(diphenylmethoxy)ethyl chloride, 14.1 g. (0.07 mole) 1-cinnamylpiperazine, 20 g., potassium carbonate powder and 250 ml. methyl isobutyl ketone was refluxed for 24 hours with stirring; after concentration, diethyl ether and water were added, the ether phase was dried on magnesium sulphate, ethereal HCl was added to a pH of 2. The dihydrochloride was filtered off and crystallized from an ethanol-ether mixture.

The impure product was treated with dilute ammonia to liberate base, which ws purified by a silicagel column with chloroform-ethylacetate (1:1) as eluent. HCl in diethyl ether was added to the appropriate fraction and crystals were precipitated from 2-propanol.

1-[2-(diphenylmethoxy)ethyl]-4-(3-phenyl-2-propenyl) piperazine dihydrochloride having a melting point of 212° C. was obtained.

EXAMPLE 16

Starting with the product of Example 10, the base was liberated with dilute ammonia. An ether solution of HCl yielded the dihydrochloride which was crystallized from 2-propanol and diethyl ether and have a melting point of 202°-203° C.

The product of Example 12 was similarly treated and crystallized from ethanol to yield a product having a melting point of 214° C.

EXAMPLE 17

The procedure of Example 9 was followed except that HCl was used instead of maleic acid. The dihydrochloride was crystallized from methanol and had a melting point of 225°-226° C.

EXAMPLE 18

A mixture of 9.5 g. (0.036 mole) 4-[3-(4-fluorophenyl)-2-propenyl]-1-piperazine-ethanol, 3.7 g. (0.018 mole) benzhydrylchloride was heated to 160° C. and kept at this temperature for half an hour. The mixture was cooled to 100° C. poured into 150 ml. of water, extracted with diethyl ether, the extract was dried on sodium sulphate and etheral HCl added. Crystals were precipitated from ethanol. The impure product was treated with dilute ammonia to liberate the base which was purified on a silicagel column with a chloroform-methanol (9:1) eluent.

The appropriate fractions were concentrated, the residue was taken up in an ethanol-diethyl ether mixture. Ethereal HCl was carefully added to a pH of 2.5; on addition of more ether, 1-[2-(diphenylmethoxy)ethyl]-4-[3-(4-fluorophenyl)-2-propenyl]piperazine dihydrochloride crystallized having a melting point of 205°-206° C.

The starting material was prepared as follows: to a mixture of 13 g. (0.1 mole) of 1-piperazine-ethanol, 15 g. (0.11 mole) of potassium carbonate and 100 ml. of ethanol, 16.2 g. (0.1 mole) of 4-fluorocinnamylchloride were added; the mixture was refluxed for 3 hours, cooled and filtered. The filtrate was concentrated, and the residue was taken up in diethyl ether, decanted and concentrated. The residue which was distilled had a boiling point of 170°-173° C./0.2 mm.

EXAMPLE 19

This example was carried out in the manner of Example 18, except that 4-(3-phenylpropyl)-1-piperazine-ethanol was used as the starting material. First, the maleate base was liberated and purified by chromatography, etc.; 1-[2-(diphenylmethoxy)ethyl]-4-(3-phenylpropyl) piperazine dihydrochloride having a melting point of 223.5° C. was obtained.

The starting material was obtained in an analogous procedure to that of the starting material of Example 18; boiling point was 160°-169° C./0.7 mm.

EXAMPLE 20

A solution of 5.2 g. of the base prepared in Example 10 in 150 ml. methanol was hydrogenated with 1 g. Pd. on charcoal. The mixture was filtered, the filtrate again hydrogenated with the same amount catalyst and the filtrate concentrated. The residue was taken up in chloroform, washed with water, dried on sodium sulphate and concentrated. The residue was taken up in diethyl ether and ethereal HCl was added to a pH of 2. The precipitate was filtered off, and recrystallized from 2-propanol and diethyl ether. 1-{2-[bis(4-fluorophenyl)-methoxy]ethyl}-4-[3-(4-fluorophenyl)propyl]piperazine dihydrochloride having a melting point of 198.0°-198.5° C. was obtained. Similarly 1-[2-(diphenylmethoxy)ethyl]-4-[3-(4-fluorophenyl)propyl]piperazine dihydrochloride was obtained.

The invention includes within its scope pharmaceutical compositions comprising, as active ingredient, at least one of the therapeutically active compounds of general formula I, or an acid addition or quaternary ammonium salt thereof, in association with a pharmaceutically acceptable carrier, diluent or excipient. The preparations may take any of the forms customarily employed for administration of therapeutic substances. Compositions for oral administration suitably contain from 5 to 100 mg of active ingredient.

Tablets and pills may be formulated in the usual manner with one or more pharmaceutically acceptable carriers, diluents or excipients, for example lactose, starch, microcrystalline cellulose (especially when direct compression is used) or highly purified silicon dioxide, and may include materials of a lubricating nature, for example calcium or magnesium stearate. Capsules made of soluble material, such as gelatin, may contain the active substance alone or in admixture with a solid or liquid diluent. Liquid preparations may be in the form of suspensions, emulsions, syrups or elixirs of the active substance in water or another liquid medium commonly used for making orally acceptable pharmaceutical formulations such as liquid paraffin, or a syrup or elixir base. Suppositories may contain the active substance in association with a suppository mass commonly used in pharmaceutical practice, such as theobroma oil, glycerinated gelatin or a high molecular weight polyethylene glycol.

The active substance may also be made up in a form suitable for parenteral administration, i.e. as a sterile solution in water or an organic solvent, or mixtures thereof, or as a suspension or emulsion in sterile water or an organic liquid usually employed for injectable preparations, for example a vegetable oil.

The invention also includes dry formulations that may be converted into a liquid composition for oral or parenteral administration by addition of a solvent or suspending liquid. such a formulation for parenteral administration may be obtained, for example, by freeze-drying an aqueous liquid medium containing an active substance, and the dry powder thus obtained may be reconstituted by adding an appropriate amount of sterile water.

The following Example illustrates the preparation of a pharmaceutical somposition according to the invention.

EXAMPLE 21

50 g. of 1-2-bis(p-fluorophenyl)methoxy ethyl-4-(3-phenylprop-2-enyl) piperazine maleate (1:2), 70 g. of microcrystalline cellulose (Avicel), 10 g. of amylum solani, 3 g. of magnesium sterate and 1 g. of highly purified silicon dioxide (Aerosil) were mixed. The mixture was then compressed into tablets of 134 mg., each containing 50 mg. of the active substance.

I claim:

1. A compound of the formula

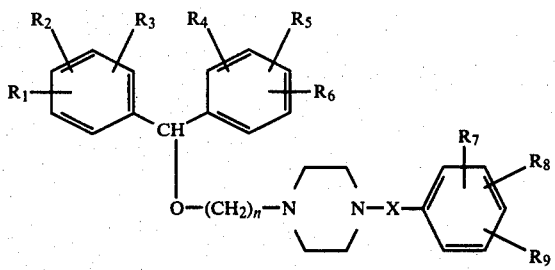

wherein $R_1$–$R_9$ are the same or different and each represents a hydrogen of halogen atom or a lower alkyl or lower alkoxy group, n is 2 or 3 and X represents the group —$CH_2$—CH═CH—, having methylene linked to the piperazine group, and nontoxic acid addition and quaternary ammonium salts thereof.

2. A compound as claimed in claim 1 in which $R_1$–$R_9$ are the same or different and each represents a hydrogen, fluorine, chlorine or bromine atom or a methyl or methoxy group and X and n are as defined in claim 1, and nontoxic acid addition and quaternary ammonium salts thereof.

3. A compound as claimed in claim 2 in which the substituents $R_1$–$R_6$ are all hydrogen.

4. A compound as claimed in claim 2 in which one or two of the substituents $R_1$–$R_6$ are fluorine or methoxy and the others hydrogen.

5. A compound as claimed in claim 4 in which said fluorine or methoxy substituents are in the para position.

6. A compound as claimed in claim 2, in which all substituents $R_7$–$R_9$ are hydrogen.

7. A compound as claimed in claim 2, in which one of the substituents $R_7$–$R_9$ is chlorine or fluorine and the other two are hydrogen.

8. A compound as claimed in claim 7, in which acid chlorine or fluorine substituent is in the para position.

9. A compound as claimed in claim 2, in which n is 2.

10. 1-[2-(diphenylmethoxy)ethoxy]-4-(3-phenyl-2-propenyl)piperazine and its nontoxic acid addition and quaternary amonium salts.

11. 1-[2-[(4-methoxyphenyl)phenylmethoxy]ethyl]-4-(3-phenyl-2-propenyl) piperazine and its nontoxic acid addition and quaternary ammonium salts.

12. 1-[2-[(4-fluorophenyl)phenylmethoxy]ethyl]-4-(3-phenyl-2-propenyl) piperazine and its nontoxic acid addition and quaternary ammonium salts.

13. 1-[2-[bis(p-fluorophenyl)methoxy]ethyl]-4-(3-phenyl-2-propenyl) piperazine and its nontoxic acid addition and quaternary ammonium salts.

14. 1-[2-[bis(4-fluorophenyl)methoxy]ethyl]-4-[3-(4-fluorophenyl)-2-propenyl]piperazine and its nontoxic acid addition and quaternary ammonium salts.

15. 1-[2-[bis(4-fluorophenyl)methoxy]ethyl]-4-[3-(4-chlorophenyl)-2-propenyl]piperazine and its nontoxic acid addition and quaternary ammonium salts.

16. A compound as claimed in claim 1 in which $R_1$ represents a halogen atom, $R_2$ and $R_3$ each represent a hydrogen or halogen atom, $R_4$, $R_5$ and $R_6$ each represent a hydrogen or halogen atom, and $R_7$ and $R_8$ and $R_9$ each represent a hydrogen or halogen atom or an alkyl group containing from one to six carbon atoms and n is 2.

17. A compound as claimed in claim 16 in which $R_1$ represents a fluorine atom in the para position, $R_4$ represents a fluorine atom in the para position or a hydrogen atom, and $R_2$, $R_3$, $R_5$ and $R_6$ each represent a hydrogen or fluorine atom.

18. A pharmaceutical composition comprising, as an active ingredient, at least one of compound claimed in claim 1 in combination with a pharmaceutically acceptable carrier.

19. A pharmaceutical composition according to claim 18, in oral dosage form, comprising from 5 to 100 mg of said active ingredient.

20. A pharmaceutical composition containing as active ingredient, a therapeutically effective amount of at least one compound of the formula:

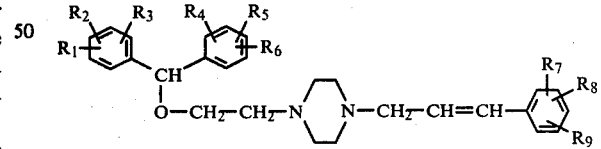

wherein $R_1$ represents a halogen atom, $R_2$ and $R_3$ each represent a hydrogen or halogen atom, $R_4$, $R_5$ and $R_6$ each represent a hydrogen or halogen atom, and $R_7$, $R_8$ and $R_9$ each represent a hydrogen or halogen atom or an alkyl group containing from one to six carbon atoms, and acid addition and quaternary ammonium salts thereof in combination with a pharmaceutically acceptable carrier.

21. A method of treating Parkinson's disease prolactin induced disorders and acromegaly which comprises administering an effective amount of a compound defined in claim 1.

* * * * *